United States Patent [19]

Hopp et al.

[11] Patent Number: 5,011,912

[45] Date of Patent: Apr. 30, 1991

[54] HYBRIDOMA AND MONOCLONAL ANTIBODY FOR USE IN AN IMMUNOAFFINITY PURIFICATION SYSTEM

[75] Inventors: Thomas P. Hopp; Kathryn S. Prickett, both of Seattle, Wash.

[73] Assignee: Immunex Corporation, Seattle, Wash.

[21] Appl. No.: 335,255

[22] Filed: Apr. 10, 1989

Related U.S. Application Data

[62] Division of Ser. No. 944,261, Dec. 19, 1986, Pat. No. 4,851,341.

[51] Int. Cl.⁵ .................... C12P 21/00; C12N 5/00
[52] U.S. Cl. ..................... 530/387; 435/70.4; 435/240.27
[58] Field of Search ............ 530/387; 435/240.27, 435/70.21

[56] References Cited

FOREIGN PATENT DOCUMENTS 035384 9/1981 European Pat. Off. .
150126 7/1985 European Pat. Off. .

OTHER PUBLICATIONS

Biotechnology Progress, vol. 5, pp. 119–125, W. H. Velander et al., Sep. 1989.
Goodman and Gilman, 4th Edition, 1970, *Pharm. Basis of Therapeutics*, pp. 948–953.
*Biochemistry*, 1970, Lehniger, A. L., pp. 149–150, Worth Publishers, New York.
Maurer et al., "Antigenicity of Polypeptides (PolyaAmino Acids): Calcium-Dependent and Independent Antibodies", *J. Immunol.* 105:567 (1970).
Frankel et al., "Hydrogen Exchange Studies of a $Ca^{++}$ Dependent Sheep HSA-Anti HSA System", *Fed. Proceed.* 36:1286 (1977).
Favre et al., "Influence of Calcium on Angiotensin II-Antibody Reaction", *Immunochemistry* 10:43 (1973).

*Primary Examiner*—Margaret Moskowitz
*Assistant Examiner*—T. M. Cunningham
*Attorney, Agent, or Firm*—Scott G. Hallquist; Christopher L. Wight

[57] ABSTRACT

A particular calcium-dependent monoclonal antibody, 4E11, is produced from a murine hybridoma cell line and is useful for purifying a recombinant fusion protein having an N-terminal identification peptide DYKDDDDK to which the monoclonal antibody binds.

4 Claims, No Drawings

HYBRIDOMA AND MONOCLONAL ANTIBODY FOR USE IN AN IMMUNOAFFINITY PURIFICATION SYSTEM

CROSS-REFERENCE TO RELATED APPLICATION

This application is a division of application Ser. No. 944,261, filed Dec. 19, 1986, now issued as U.S. Pat. No. 4,851,341.

BACKGROUND OF THE INVENTION

The present invention relates to immunoaffinity chromatography systems, and particularly to immunoaffinity processes employing a monoclonal antibody having divalent cation-dependent affinity for a selected peptide determinant.

The prior art describes recombinant fusion proteins which comprise synthetic leader peptides or protein fragments linked to independently derived polypeptides. In such fusions, the leader peptide or protein fragment can facilitate protein expression and purification by providing, for example, enzymatic activity enabling identification of recombinants, an amino acid sequence recognized by cellular secretory mechanisms, or a sequence having distinctive chemical or antigenic characteristics useful in purifying the fusion protein by ion exchange, reverse phase, or affinity chromatographic media.

Itakura, U.S. Pat. No. 4,571,421, described hybrid polypeptides consisting of a somatostatin sequence and a fragment of β-galactosidase enzyme, separated by a CnBr-cleavable site permitting separation of the two protein segments. In this system, the presence of the β-galactosidase fragment permits identification of recombinants bearing the somatostatin sequence. Schuman et al., *J. Biol. Chem.* 255:168 (1980), and Reed et al., *Gene* 20:255 (1982) disclose variations of this approach involving fusion of nucleotide sequences encoding biologically active fragments of β-galactosidase and newly isolated genes. The translated hybrid protein was isolated by reference to the physical and enzymatic properties of β-galactosidase, and used to prepare specific antisera to the product of the newly isolated genes.

Rutter, Published European Patent Application No. 35384 (1981), discloses DNA constructions used to facilitate expression of cloned DNA sequences. Among the constructions disclosed are sequences encoding fusion proteins comprising an N-terminal sequence having distinctive physical properties useful for purification, joined to a desired C-terminal portion via a sequence which can be specifically cleaved to remove the N-terminal sequence. An example of such a cleavage sequence is the peptide sequence DDDDK recognized by enterokinase. Sequences having particular properties useful for purification include polyanionic segments and polycationic segments that will bind readily to ion exchangers, and hydrophobic segments capable of binding to reverse-phase media. This reference also discloses hybrid fusion proteins comprising fragments capable of being bound by specific antibody in an affinity chromatography step.

Brewer et al., U.S. Pat. No. 4,532,207, disclose recombinant fusion proteins comprising a charged polymer of amino acids, for example, polyarginine, linked to a polypeptide of interest. Following expression in a microbial host, the fusion protein is purified by chromatography involving binding of the charged polymer to ion-exchange media. Following purification, the charged polymer is removed by controlled digestion with an exopeptidase. Smith et al., *Gene* 32:321 (1984) and Sassenfeld, *Bio/Technology*, January 1984, p. 76, also describe aspects of this approach to recombinant protein purification.

Improvements in recombinant protein expression and purification technologies are of considerable interest to the biotechnology, pharmaceutical, and chemical industries.

SUMMARY OF THE INVENTION

The present invention provides a murine hybridoma and a monoclonal antibody produced therefrom. The monoclonal antibody is a divalent cation-dependent antibody and is used in a process for purifying a recombinant fusion protein having a terminal identification sequence comprising multiple anionic amino acid residues. The process comprises forming a complex of the protein with the monoclonal antibody which is specific for the sequence, isolating the complex, and dissociating antibody and protein by selectively depleting the concentration of divalent cations in contact with the complex.

DETAILED DESCRIPTION OF THE INVENTION

The present invention provides an efficient process for protein isolation, utilizing an identification peptide having multiple anionic amino acid residues in conjunction with a cation-dependent monoclonal antibody. Such a peptide provides a highly immunogenic peptide determinant, and the presence of multiple anionic amino acid residues facilitates isolation of cation-dependent antibodies. Although both natural and synthetic anionic amino acids could conceivably be incorporated into identification peptides, aspartic acid and glutamic acid are preferred. Being natural amino acids, they can be expressed as components of recombinant polypeptides in conventional protein translation systems. Generally, terminal identification peptides comprising from 3 to 6 aspartic acid or glutamic acid residues, or mixtures thereof, are useful.

A particularly preferred embodiment of this concept involves use of the amino acid sequence Asp-Tyr-Lys-Asp-Asp-Asp-Asp-Lys, or DYKDDDDK, as an N-terminal identification peptide. This sequence is immunogenic and comprises an enterokinase recognition site. Fusion proteins expressed with an N-terminal DYKDDDDK "flag" can be purified using immobilized monoclonal antibody which specifically recognizes the flag determinant. If desired, the flag sequence can be cleaved from the remainder of the fusion protein using enterokinase; this cleavage step can be undertaken before or after separation of the bound flag ligand from the immobilized antibody.

Conventional recombinant DNA techniques are employed to construct DNA vectors encoding fusion proteins having N-terminal or C-terminal identification peptides, for example, the N-terminal DYKDDDDK flag, coupled to a polypeptide sequence to be isolated. Following expression in cultures of transformed organisms, the fusion proteins can be separated from crude extracts or culture supernatants in a single affinity step mediated by specific anti-flag antibody. The DYKDDDDK flag provides superior identification and purification performance due to the presence of both hydrophilic and aromatic residues. This combination renders flag constructions highly immunogenic and ensures that the flag determinant, even when conjugated to much larger protein molecules, remains accessible to antibody in aqueous media under physiological conditions. Additional information regarding the DYKDDDDK flag system is provided in European Pat. application No. EP-A-0150126.

The improvement which characterizes this invention is an antibody-antigen system in which binding is dependent upon the presence of divalent metal cations. In a particularly preferred embodiment, the calcium-dependent anti-flag monoclonal antibody produced by the hybridoma cell line designated 4E11, which is specific for DYKDDDDK flag peptide, is employed. This cell line has been deposited on Nov. 12, 1986 with the American Type Culture Collection (ATCC), 12301 Parklawn Drive Rockville, Md., 20852 USA, under accession number HB-9259. Although calcium-dependent antibodies have previously been reported, [see. e.g., Maurer et al., *J. Immunol.* 105:567 (1970), and Maurer et al., *Methods Enzymol.* 70:49 (1980)] their use as immunoaffinity reagents has not been disclosed.

Cation-dependent affinity media bind ligand securely only in the presence of appropriate cation, and can be induced to release ligand by selectively depleting the concentration of divalent metal cations in contact with the complex of immobilized antibody and ligand. This can be achieved by simply washing the affinity media with a solution lacking the particular cation, or preferably, by eluting with a chelating agent such as an EDTA salt (ethylene diamine tetraacetic acid), or EGTA (ethylene glycol-bis($\beta$-aminoethyl ether) N,N,N',N'-tetraacetic acid). This approach avoids use of affinity elution methods employing high salt, low pH, or chaotropic agents, which may be irreversibly denaturing. Since elution by cation removal or depletion is highly specific for the flag-antibody complex, the recovered protein is less likely to be contaminated by extraneous proteins bound to the affinity column at sites other than the antibody combining site.

The media employed to immobilize the cation-dependent antibody can be agarose, Sepharose, acrylamide, cellulosic materials, or other suitable matrices known to those of skill in the art. Preferably, antibody is covalenty bonded to media, for example, by coupling to Sepharose (Pharmacia, Uppsala, Sweden) or Affi-Gel-10 (Bio Rad Laboratories, Richmond, Calif., USA) using a procedure involving reaction of free amino groups with N-hydroxy-succinimide esters. Kits for this purpose are commercially available; a convenient method is disclosed by Wilchek et al., *Biochemistry* 10:2828 (1971). Immunoaffinity purification procedures employed in connection with the system disclosed herein can be by batch or column chromatographic methods. In addition, numerous immunoassays for expressed fusion proteins can be devised, relying upon the specificity of the divalent cation-dependent antibody for the flag determinant.

Depending upon the particular characteristics of the monoclonal antibody which is isolated, various divalent cations may be suitable in effecting binding of antibody to antigen. Such cations could include $Ca^{++}$, $Mg^{++}$, $Mn^{++}$, $Cu^{++}$, $Ni^{++}$, $Zn^{++}$, $Cd^{++}$, $Ba^{++}$ or $Sr^{++}$. Of the foregoing, $Ca^{++}$ is more commonly found to mediate cation-dependent binding sensitivity and is therefore preferred. Generally, cation concentrations should be at least 0.3 to 1 mM to ensure effective binding. Use of an EDTA solution of at least 0.5 mM as eluant, or alternatively, a concentration greater than the effective concentration of cation, effectively reduces cation concentration to a level enabling protein release.

SYNTHESIS OF PEPTIDE IMMUNOGEN

Synthetic identification peptides can be conjugated to fatty acid-derivatized amino acids to prepare peptide immunogens, which are presented to mice to raise anti-peptide antibodies. The fatty acid-derivatized amino acids are added to the C-terminal region of the peptides, in order that the resulting peptides form micelles in aqueous media. The linear, hydrophobic fatty acid chains form the micelle nucleus, while the more hydrophilic N-terminal portions of the ligand peptides are presented to antibody on the micelle periphery.

One or more amino acids can be used as spacers to separate the hydrophilic residues from the derivatized residues. Preferably, one to six neutral amino acids, selected from the group consisting of Gly, Pro, or Ser, are employed for this purpose. The amino acids to be derivatized to fatty acids are preferably selected from the group consisting of lysine and ornithine, and can be from 1 to 3 in number. Palmitic, oleic, and stearic acids are useful fatty acids; palmitic acid is preferred. The peptide antigen can be synthesized by any suitable method, for example, the Merrifield solid phase method widely employed in connection with automated peptide synthesizers. A suitable method is detailed in copending European Pat. application No. EP-A-0150126.

Alternatively, the identification peptide can be conjugated to a carrier polypeptide or protein to provide a flag immunogen. Suitable carrier proteins include globulin fractions, the serum albumins of various species, hemocyanin, ovalbumin, lactalbumin, thyroglobulin, fibrinogen, or synthetic polypeptides, for example poly(L-lysine). The number of haptens bound to the carrier protein can vary from 2 to 50, depending upon the conditions of conjugation. Preferably, a given carrier has, on average, at least five peptide haptens covalently attached. Generally, higher antibody titers are obtained using conjugates having higher epitope densities. Suitable methods for hapten-carrier conjugation are disclosed by Bauminger et al., *Methods in Enzymology* 70:151 (1980); Reichlin, *Methods in Enzymology* 70:159 (1980); Kitagawa et al., *J. Biochem.* 94:1165 (1983); and various references reviewed by Lerner, *Nature* 299:592 (1982).

PREPARATION OF MONOCLONAL ANTIBODIES

The derivatized or conjugated peptide immunogen is employed to generate monoclonal antibodies against the peptide hapten using conventional techniques, for example, those disclosed in U.S. Pat. No. 4,411,993. In this method, the immunogen is emulsified in complete Freund's adjuvant and injected in amounts ranging from 10-100 $\mu$g subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with the immunogen in the presence and absence of calcium or other divalent metal cations. Generally, metal cation concentrations in the range 0.1-10 mM are suitable. Methods for ELISA are disclosed by Engvall et al., *Immunochemistry* 8:871 (1971) and in European Pat. application No. EP-A-0150126. Positive clones are then injected into the peritoneal cavities of syngeneic Balb/c mice to produce ascites containing high concentrations (>1 mg/ml) of anti-peptide monoclonal antibody. The resulting monoclonal antibody can be purified by ammonium sulfate precipitation followed by gel exclusion chromatography, and/or affinity chromatography based on binding of antibody to Protein A of *Staphylococcus aureus*, or binding to immobilized identification peptide.

The following examples illustrate particular aspects of the present invention:

EXAMPLE 1: PREPARATION OF 4E11 ANTIBODY AFFINITY MEDIA

A murine hybridoma clone, designated 4E11, was isolated by screening for monoclonal antibody capable of specifically binding the DYKDDDDK flag fused to the N-terminus of human interleukin-2 (IL-2). Antibody-containing ascites produced by injection of the 4E11 hybridoma into syngeneic mice were purified and concentrated by standard methods including ammonium sulfate precipitation, affinity chromatography, and ultrafiltration. 10 ml of a purified, concentrated protein solution containing about 2.6 mg/ml 4E11-monoclonal antibody were dialyzed against 4 liters 0.1M HEPES buffer, pH 7.5, at 4° C. After about 48 hr and three changes of dialysis buffer, the contents of the dialysis tubing (about 7.5 ml) were transferred to a 50 ml polypropylene tube and held at 4° C. Affi-gel-10 ($\omega$-aminohexyl agarose; Biorad, Richmond, Calif., U.S.A.) was transferred to a sintered glass funnel and washed extensively with isopropanol followed by deionized water. Approximately 10 ml of the washed gel were added to the tube containing the antibody solution and reacted overnight on a rotator at 4° C., in accordance with the manufacturer's instructions. The following day, unreacted sites on the affinity media where blocked by adding 100 $\mu$l of 1M glycine ethyl ester, pH 8, to the media, and gently agitating for 1.5 H at 4° C.

The resulting antibody-coupled gel, containing approximately 3.2 mg antibody/ml of gel, was washed with phosphate-buffered saline (PBS; 0.145M NaCl, 0.016M KHPO$_4$, pH 7.0) followed by PBS/0.02% sodium azide, and then stored at 4° C.

EXAMPLE 2: PURIFICATION OF FLAG-BPA FUSION PROTEIN

A yeast expression plasmid, pBC65, was constructed, comprising DNA sequences from pBR322 for selection and replication in *E. coli* (Ap$^r$ gene and origin of replication) and yeast DNA sequences including the TRP1 gene as a selectable marker and the yeast 2$\mu$ origin of replication. pBC65 also includes a glucose-repressible alcohol dehydrogenase 2 (ADH2) promoter, and an $\alpha$-factor leader sequence enabling secretion of heterologous proteins from a yeast host. Fused in-frame to the $\alpha$-factor leader was an inserted DNA sequence encoding a flag fusion protein comprising the DYKDDDDK sequence linked to a cDNA encoding putative human BPA (burst-promoting factor) protein. *S. cerevisiae* strains 79 and XV2181 (Trp$^-$) were transformed with pBC65 by the method of Hinnen et al., *Proc. Natl. Acad. Sci. U.S.A.* 75:1929 (1978), selecting for Trp$^+$ transformants. Transformants of each yeast strain were cloned and grown for expression in a rich medium consisting of 1% yeast extract, 2% peptone, and 1% glucose supplemented with 80 $\mu$g/ml adenine and 80 $\mu$g/ml uracil. Derepression of the ADH2 promoter and expression of the fusion protein was induced upon exhaustion of medium glucose. Crude yeast-conditioned supernatant was collected from the fermentation mixtures by filtration and held at 4° C. until needed.

5 ml of the 4E11 antibody-coupled affinity gel slurry prepared as described in Example 1, above, were added to a polypropylene column to provide a bed volume of about 1.5 ml. The column was then flushed with 15 ml PBS, followed by 15 ml 0.1M glycine-HCl, pH 3.0, and finally 25 ml PBS.

70 ml of the 79:pBC65 yeast-conditioned supernatant were treated by adding 7 ml 10x PBS, raising the pH of the extract to 7.12. The resulting buffered yeast supernatant was applied to the 4E11 immunoaffinity column in two 10 ml aliquots. Following sample application, the column was washed with 9 ml PBS, and stored at 4° C. overnight. The column was eluted with five 1 ml additions of 0.1M glycine-HCl pH 3.0, while collecting 1 ml fractions. After elution, the column was extensively washed with PBS and stored at 4° C. in PBS/0.02% sodium azide.

Samples of the wash and elution fractions were analyzed by SDS-PAGE in conjunction with Western immunoblots using silver staining of gels and 4E11 antibody. The Western transfer indicated the presence of 4E11-reactive material having an apparent molecular weight of about 28,000 daltons in the wash fractions, indicating lack of binding.

The 4E11 immunoaffinity column was then prepared for a second trial in which the wash buffers used in connection with one of the yeast supernatants was supplemented to contain 0.5 mM MgCl$_2$ and 1.0 mM CaCl$_2$. In this second experiment, approximately 112 ml of the 79:pBC65 yeast supernatant (pH 7.04) was applied to the column in 2 10 ml aliquots. The column was washed with PBS containing 0.5 mM MgCl$_2$/1.0 mM CaCl$_2$. The column was eluted with 0.1M glycine-HCl as before. SDS-PAGE/Western analysis of the collected fractions indicated that the 4E11-reactive material was bound until elution with glycine-HCl. The majority of the yeast proteins were removed from the column in the wash fractions.

EXAMPLE 3: PURIFICATION OF FLAG-GM-CSF FUSION PROTEIN

A yeast expression vector, comprising DNA coding for the DYKDDDDK sequence fused to DNA encoding mature human granulocyte-macrophage colony stimulating factor (GM-CSF), was constructed as follows.

A 417 base pair AhaII-NcoI fragment containing the majority of the coding region and part of the 3' flanking region of the wild-type human GM-CSF gene was excised from plasmid pYαfHuGM to provide a fragment lacking the sequence corresponding to the N-terminal 24 amino acids of the mature protein. This portion of the gene was reconstituted using an oligonucleotide which provides a revised 5' nucleotide sequence encoding an amino acid sequence coincident with the first 22 amino acids of the mature protein, but containing a 5' KpnI terminal restriction site, a BglII site at amino acid codon 4, a second NcoI site at amino acid codon 12, HpaI and HindIII sites at codons 16 and 21, respectively, and a codon substitution to provide a leucine residue at position 23. The sequence of the linker appears below:

```
                       Ala Pro Ala
    5'-CT TTG GAT AAA AGA GCT CCA GCT
    3'-CAT GGA AAC CTA TTT TCT CGA GGT CGA
       KpnI

Arg Ser Pro Ser Pro Ser Thr Glu Pro Trp
    AGA TCT CCA TCT CCA TCT ACT CAA CCA TGG
    TCT AGA GGT AGA GGT AGA TGA GTT GGT ACC
    BglII                                NcoI

Glu His Val Asn Ala Ile Glu Glu Ala
    GAA CAC GTT AAC GCT ATT CAA GAA GCT
    CTT GTG CAA TTG CGA TAA GTT CTT CGA
            HpaI                HindIII Leu
                                   TTG-3'
                                   AAC GC-5'
                                      AhaII→
```

The resulting construct was cloned into KpnI and NcoI-cut plasmid pBC11 (a pBR322 derivative) to generate plasmid pBC25. This plasmid is a *S. cerevisiae* expression vector substantially similar to pYαfHuGM, except for substitution of the glucose-repressible alcohol dehydrogenase 2 (ADH2) promoter for the α-factor promoter of pYαfHuGM. pBC25 was then cut with KpnI and BglII and ligated to the following oligonucleotide, which provides a DNA sequence encoding a 3' fragment of the yeast α-factor leader sequence, fused in-frame to an *S. cerevisiae* KEX2 protease recognition site, the flag identification peptide, and the first 3-5 amino acids of mature human GM-CSF:

```
       Leu Asp Lys Arg
    5'-CT TTG GAT AAA AGA
    3'-CAT GGA AAC CTA TTT TCT
       KpnI

|←———— flag determinant ————→|
    Asp Tyr Lys Asp Asp Asp Asp Lys
    GAC TAC AAG GAC GAC GAT GAC AAG—
    CTG ATG TTC CTG CTG CTA CTG TTC—
    ↑                         ↑
    KEX2                      Enterokinase
    Cleavage                  Cleavage Ala Pro Ala
                       GCT CCA GCT A-3'
                       CGA GGT CGA TCT AG-5'
                                      BglII
```

Using this vector, a fusion protein comprising the flag determinant linked to the N-terminal alanine of mature human GM-CSF is expressed and secreted by a yeast host. The α-factor secretory mechanism cleaves the translated polypeptide following the Lys-Arg KEX2 recognition site. This vector was used to transform yeast strain XV2181 by standard methods, selecting for Trp+ transformants in a selective medium consisting of 0.67% yeast nitrogen base, 0.5% casamino acids, 2% glucose, 10 μg/ml adenine and 20 μg/ml uracil.

Transformed yeast were grown in rich medium (1% yeast extract, 2% peptone, and 1% glucose supplemented with 80 μg/ml adenine and 80 μg/ml uracil) at 30° C. After removing yeast by centrifugation, the resulting conditioned medium was prepared for assay by filtering through a 0.45μ cellulose acetate filter.

5 ml of the 4E11 antibody immunoaffinity gel slurry, prepared as described in Example 1, above, were transferred to a polypropylene column, providing a bed volume of about 1.5 ml. The column was flushed with 15 ml PBS, followed by 15 ml 0.1M glycine-HCl, pH 3, and then an additional 30 ml PBS.

11 ml of 10x PBS were added to 100 ml of yeast extract, raising the pH to about 6.9. 30 ml of the resulting diluted yeast extract were applied to the immunoaffinity column, which was then washed with five 1 ml aliquots of PBS/1 mM $CaCl_2$, with 5 minute intervals between aliquots. Fractions were collected from each application. The column was then eluted with 1.5 ml PBS, followed by four additional aliquots, each 1 ml, of PBS added hourly. 1.5 ml of PBS containing 10 mM EDTA was then added, followed by four additional 1 ml aliquots of PBS/10 mM EDTA at hourly intervals. Finally, 4 ml glycine-HCl, pH 3, were added and collected as one fraction, which was neutralized by addition of 50 μl 1M Tris-HCl, pH 7.0. All fractions were then analyzed by SDS-PAGE followed by silver staining. The results indicated that the majority of the proteins and other contaminants present in the yeast supernatant eluted from the column in the initial wash employing PBS/1.0 mM $CaCl_2$, while the flag-GM-CSF fusion protein remained bound. The fusion protein eluted in a relatively sharp peak in the initial wash with PBS lacking $Ca^{++}$ ion. A small amount of additional material of the proper molecular weight was observed to elute from the column when the PBS/EDTA solution was applied.

The foregoing experiment was repeated substantially as described above, except that the fusion protein was eluted from the column by application of a PBS/10 mM EDTA solution following washing with PBS/1 mM $CaCl_2$. In this experiment, all detectable 4E11-reactive material eluted from the column in a sharp peak upon application of the PBS/EDTA eluant, free of other protein contaminants.

What is claimed is:

1. Murine hybridoma 4E11 (ATCC HB 9259).

2. A monoclonal antibody having essentially the same binding affinity and epitopic specificity of a monoclonal antibody secreted by murine hybridoma 4E11 (ATCC HB 9259).

3. A monoclonal antibody that binds the peptide DYKDDDDK only in the presence of a divalent metal cation selected from the group consisting of $Ca^{++}$, $Mg^{++}$, $Mn^{++}$, $Cu^{++}$, $Ni^{++}$, $Zn^{++}$, $Cd^{++}$, and.

4. A monoclonal antibody according to claim 3 that binds the peptide DYKDDDDK in the presence of $Ca^{++}$.

* * * * *

UNITED STATES PATENT AND TRADEMARK OFFICE
CERTIFICATE OF CORRECTION

PATENT NO.   :   5,011,912

DATED        :   April 30, 1991

INVENTOR(S)  :   Thomas P. Hopp; Kathryn S. Prickett

It is certified that error appears in the above-identified patent and that said Letters Patent is hereby corrected as shown below:

Column 1, line 30:   "described" should read --describes--

Column 8, line 63:   Delete ",and"

Column 8, line 63:   After "Zn++ " add --and--

Signed and Sealed this

Twentieth Day of October, 1992

Attest:

DOUGLAS B. COMER

Attesting Officer         Acting Commissioner of Patents and Trademarks